United States Patent [19]

Noettling

[11] Patent Number: 5,764,719
[45] Date of Patent: Jun. 9, 1998

[54] C-FRAME X-RAY DIAGNOSTIC DEVICE FOR PRODUCING TOMOGRAPHIC RECORDINGS

[75] Inventor: Alois Noettling, Pottenstein, Germany

[73] Assignee: Siemens Aktiengesellschaft, Munich, Germany

[21] Appl. No.: 614,625

[22] Filed: Mar. 13, 1996

[30] Foreign Application Priority Data

Mar. 13, 1995 [DE] Germany ............ 195 09 007.1

[51] Int. Cl.⁶ .................................. A61B 6/03
[52] U.S. Cl. ................................... 378/4; 378/901
[58] Field of Search .................. 378/4, 15, 17, 378/901

[56] References Cited

U.S. PATENT DOCUMENTS

| | | | |
|---|---|---|---|
| 5,014,293 | 5/1991 | Boyd et al. | 378/197 |
| 5,485,492 | 1/1996 | Pelc | 378/5 |
| 5,583,901 | 12/1996 | Reitter et al. | 378/4 |

FOREIGN PATENT DOCUMENTS

| | | |
|---|---|---|
| 3037471 | 5/1982 | Germany . |
| 3419043 | 11/1985 | Germany . |
| 4402240 | 8/1994 | Germany . |

*Primary Examiner*—David P. Porta
*Assistant Examiner*—David Vernon Bruce
*Attorney, Agent, or Firm*—Sughrue, Mion, Zinn, Macpeak & Seas, PLLC

[57] ABSTRACT

A device and a process for producing tomograms by means of an X-ray diagnostic device which has a C-frame-like mount (7) on which a radiation transmitter (5) and a planar detector as radiation receiver (6) are arranged at opposite ends facing each other. Various signals stored in memory (17, 18, 19, 27) are used by a signal processing device (4) in the calculation of processed image signals. These signals include signals ($I_p$) relating to the central point of rotation (31) for the scanning operation, and signals ($\Delta S$, $\Delta U$) for correction geometric distortions and/or vignetting effects and/or the film-focus distance.

43 Claims, 8 Drawing Sheets

5,764,719

C-FRAME X-RAY DIAGNOSTIC DEVICE FOR PRODUCING TOMOGRAPHIC RECORDINGS

FIELD AND BACKGROUND OF THE INVENTION

The invention relates to an X-ray diagnostic device capable of producing tomographic recordings and having a recording unit which has a C-frame-like mount arranged to support a radiation transmitter, for transmitting a beam of radiation, and a radiation receiver, arranged opposite the radiation transmitter, for receiving the beam of radiation and for producing electric signals.

An X-ray diagnostic device described in German Laid-Open Publication No. 30 37 471 A1 has a supporting device for an object to be examined. It also has means for producing a relative displacement between the recording unit and the supporting device for the purpose of performing a radiation scan of the object to be examined in a cross-sectional plane. A computer calculates a transverse tomogram of the cross-sectional plane from the output signals of the radiation receiver.

SUMMARY OF THE INVENTION

It is an object of the present invention to improve an X-ray diagnostic device of the type mentioned above in particular such that the image quality is enhanced. A further object of the invention is providing a more versatile C-frame X-ray diagnostic device than previously known.

These and other objects are achieved by means of the present invention, as defined by various appended independent claims. Thus, in order to accomplish the above-mentioned objects, the invention provides an X-ray diagnostic device having a recording unit that has a C-frame-like mount on which there are arranged a radiation transmitter, for transmitting a beam of radiation, and a radiation receiver, arranged opposite the radiation transmitter, for receiving the beam of radiation and for producing electric signals. Further, according to the invention, certain of the signals used for producing the image signals are signals which are stored in a memory and relate to the central point of rotation of the radiation scan. Additional signals that also can be utilized for producing the image signals include signals, stored in memory, for correcting vignetting effects and/or geometric distortions. Blurriness of the image, caused by the device, can thus advantageously be reduced in the construction on a tomogram on a display device.

It is particularly advantageous if the computing unit used for calculating the image signals evaluates input signals obtained during a radiation scan of a test object with regard to their maximum spacing from one another and calculates a mean spacing signal therefrom. This calculated mean spacing signal is also preferably stored in memory. In this way, the above-mentioned central point of rotation can be determined even if the object to be examined and/or the supporting device have no defined or established relationship to the recording unit.

In order to check whether the signals obtained during a radiation scan of a test object are actually at their maximum spacing from one another, it is advantageous if the computing unit checks, on the basis of radiation direction signals, whether the signals of the maximum spacing are produced at radiation directions offset by 180°.

As mentioned above, in order to improve the tomogram quality further, it is advantageous to store in a memory signals for correcting vignetting effects and/or for correcting geometric distortions and to use these in the calculation of the image signals.

In accordance with another aspect of the invention, a process for operating the X-ray diagnostic device is provided, wherein, in one step of the process, signals that are stored in a memory and relate to the central point of rotation and/or signals for correcting vignetting effects and/or signals for correcting geometric distortions are used in the calculation of the image signals.

According to yet another aspect of the invention, a process for operating the X-ray diagnostic device is provided, wherein, in one process step, signals from at least two rows of a planar detector are received. Respective pixel signals selected from these rows so as to all correspond to the same given column can then be used to calculate averaged pixel signals corresponding to the respective pixel signals.

BRIEF DESCRIPTION OF THE DRAWINGS

Further advantages and details of the invention will become apparent from the following description of preferred embodiments, with reference to the drawings, in conjunction with the dependent claims. In the drawings:

DETAILED DESCRIPTION OF THE PREFERRED EMBODIMENTS

Figure 1:
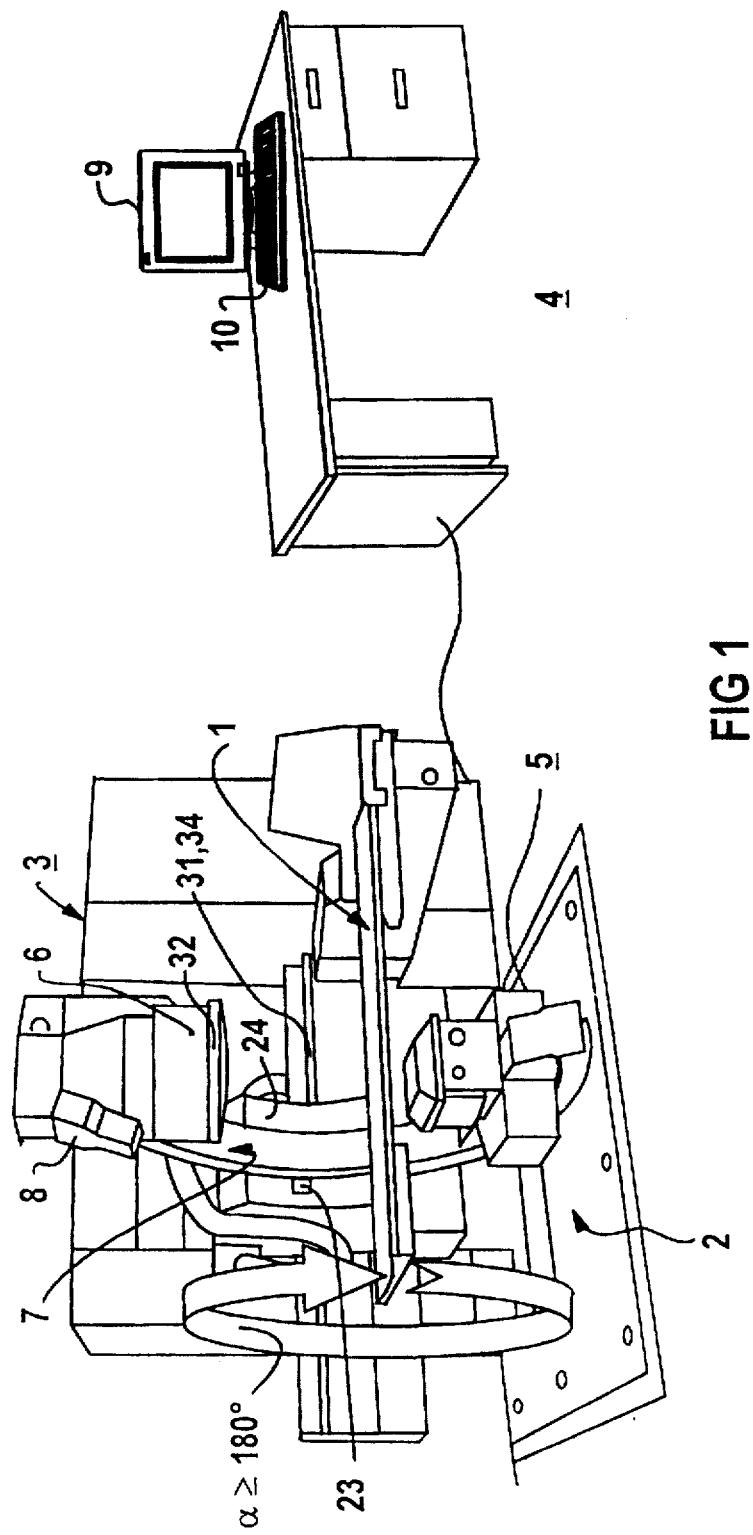
FIG. 1 is a schematic diagram of an X-ray diagnostic device according to a first embodiment the invention in a basic representation.

FIG. 1 shows a first preferred embodiment of an X-ray diagnostic device according to the invention, which has a supporting device 1 for an object to be examined (e.g., a patient), a recording unit 2, control and regulation devices 3 and a signal processing device 4. The recording unit 2 has a radiation transmitter 5 for transmitting a beam of radiation and a radiation receiver 6, arranged opposite the transmitter, for receiving the beam of radiation. In the embodiment, the radiation transmitter 5 and the radiation receiver 6 are located at the ends of a C-frame-like mount 7. Using displacing means, the recording unit 2 can thus be driven through at least 180° about the longitudinal axis of the supporting device 1.

Connected downstream of the radiation receiver 6, which is designed, for example, as an image intensifier, is a television camera 8 to convert the plurality of radiation shadows produced during the scanning of an object being examined into electric signals. The electric signals produced by the television camera 8 are then fed as video signals for further processing to the signal processing device 4, in particular, for producing an image. The device 4 is connected to a monitor 9 for displaying the image. An input device 10 is provided to control, if necessary, the radiographic procedure, with respect to the scanning operation itself and for entering various recording and processing parameters. The input device 10 acts on the signal processing device 4 and, via the signal processing device 4, on the control and regulation device 3.

To further explain the invention, reference is now made to FIGS. 2 to 10. In these figures, elements which have already been provided with reference symbols in FIG. 1 are identified by the same reference symbols.

Pre-Processing: Geometric Distortions

A beam of radiation 11, originating from the radiation transmitter 5, preferably in a fan shape, is in this case incident on a test object 12, which has regions 13, 14 of different radiation absorption. The test object 12 can for this purpose be produced from plastic into which lead wires have been incorporated as regions 13 of high radiation absorption. The lead wires can be arranged e.g., as parallel lines, or as a grid, or in some other pattern. As an aside, while the discussion that follows below refers generally to lead wires, it is also possible to produce the test object 12 from material which essentially absorbs radiation, and to incorporate therein linear or grid-shaped apertures having a particular pattern as low radiation absorption regions 14.

Figure 3:
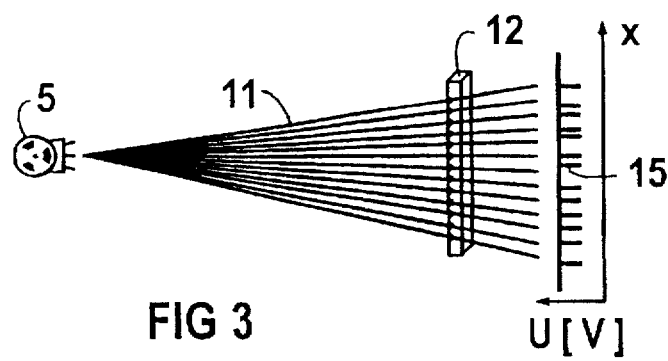
FIG. 3 shows an example of the actual spacing signals which are produced by the test object and which can be derived from a row of the radiation receiver.

The radiation shadow from the test object 12 is incident on the radiation receiver 6 of which, for the purpose of simplifying the explanation, only one row 6a for producing electric signals is to be considered. The output signal of the row 6a of the radiation receiver 6 is shown in a simplified representation in FIG. 3. It can readily be seen that, as a result of the pattern defined by the test object, signal amplitudes 15 are produced which are spaced apart from one another. In the case of error-free imaging of the test object 12, the spacings should be equal if the lead wires (or apertures) also have the same spacing from one another. In FIG. 3, however, it is shown that the signal amplitudes 15 have different spacings despite identical spacings of the lead wires.

Figure 2:
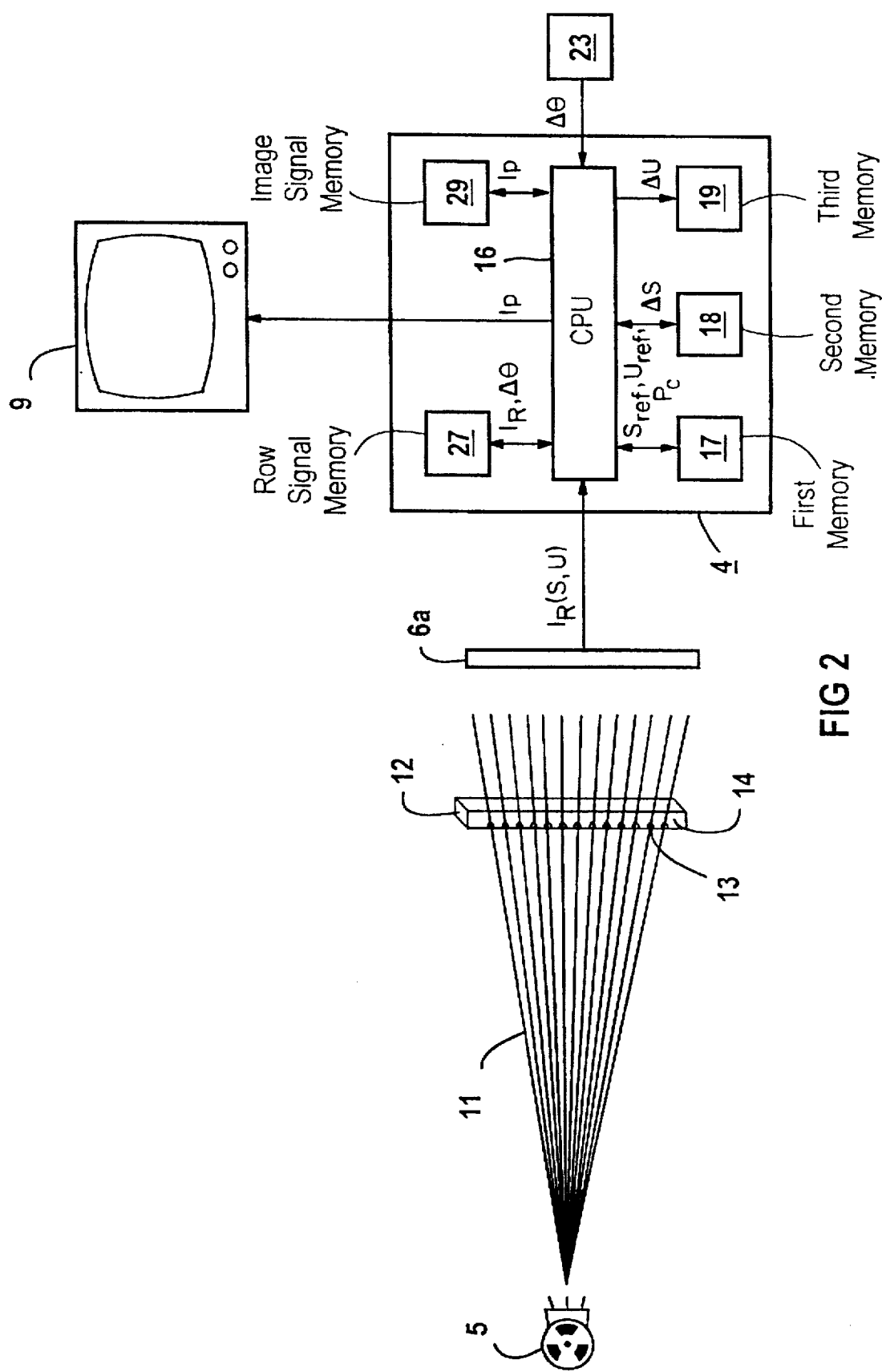
FIG. 2 shows a test object and a signal processing device of the X-ray diagnostic device according to FIG. 1 in block diagram form.

According to one embodiment of the invention, for the purpose of correcting geometrical distortions such as those just described, the signal processing device 4 shown FIG. 2 is provided with a computing unit in such as a CPU 16, and two memories 17, 18. Reference spacing signals $S_{ref}$ representing desired spacings are stored in the first memory 17, which signals would result on the basis of the projection of the test object 12 onto the radiation receiver 6 in the case of ideal, that is to say error-free, imaging. In this case it is irrelevant whether the lead wires have the same or different spacing, if appropriate reference spacing signals are stored. The CPU 16 compares the actual spacing signals S (shown at 15 in FIG. 3) originating from the radiation receiver 6, 6a with the reference spacing signals $S_{ref}$ and produces correction signals ΔS directed to eliminating any difference between respective actual and reference spacing signals. These correction signals can then be stored in the second memory 18 and taken into account to eliminate non-linearities in calculating image information and displaying an image on the monitor 9. While the preferred embodiment makes use of two memories 17, 18, alternative embodiments could utilize merely a single memory or more than two memories.

However, the lead wires of the test object 12 preferably have an at least approximately equal spacing. If this is the case, the CPU 16 can then be fashioned to calculate a signal $S_{av}$ of a mean spacing between lead wires from the actual spacing signals originating from the radiation receiver 6, 6a and to form correction signals ΔS' from the difference between the respective actual spacing signals S and the signal of the mean spacing $S_{av}$, said correction signals ΔS' being stored in the second memory 18. In this case, the first memory 17 can then be dispensed with.

The radiation receiver 6 is a planar detector such as, for example, a image intensifier or a semiconductor detector. These planar detectors have individual detector cells, which are selected pixel by pixel and row by row to output pixel signals. According to one method of implementing the above, the CPU 16 preferably counts the incoming number of pixel signals between the signal amplitudes 15 as the actual spacing signals S and calculates therefrom the mean number of pixel signals indicative of the reference spacing signals $S_{ref}$. The respectively counted pixel signals between two signal amplitudes 15 are then compared with the calculated mean number of pixel signals. If the number of pixel signals between two signal amplitudes 15 is greater than the calculated mean number of pixel signals, the number of pixel signals is then appropriately reduced and, if the number is smaller than the calculated mean number of pixel signals, the number of pixel signals is then appropriately increased. The values which are deleted or inserted are stored as correction signals in the second memory 18 and are used in constructing an image.

B. Pre-Processing: Vignetting Effects

Figure 4:
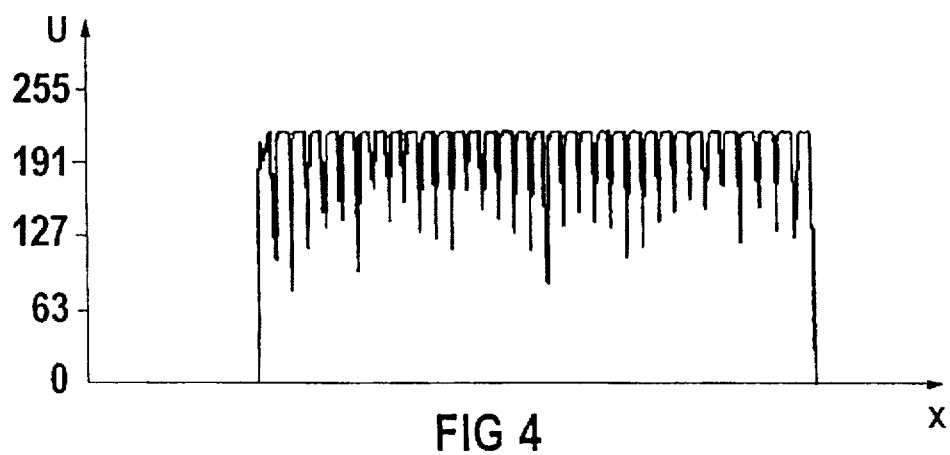
FIG. 4 shows the actual spacing signals which are produced by the test object and which can be derived from a row of the radiation receiver, without vignetting correction.

By means of the signal processing device 4, it is possible to evaluate and correct not only the spacing of the signal amplitudes 15 from one another but also the signal level. In FIG. 4, a signal of the scanned row 6a of the radiation receiver 6 is shown. It can be seen that the signal amplitudes have different respective levels, which can be caused by vignetting effects or by the radiation conversion system. According to one preferred method of correcting these vignetting effects, the radiation absorption of the lead wires (regions 13) and of the regions 14, respectively, should be at least approximately equal. The signals originating from the radiation receiver 6 or 6a during the radiography are fed to the CPU 16 and are evaluated with regard to their actual signal level U. A mean reference signal level $U_{av}$ is calculated from the actual signal levels, and correction signals ΔU are formed from the difference between the respective actual signal level U and the reference signal level $U_{av}$ and are stored in a further memory 19. However, it is also possible to store at least one predetermined reference signal level $U_{ref}$ for example in the memory 17, and to use this in producing the correction signals.

Figure 5:
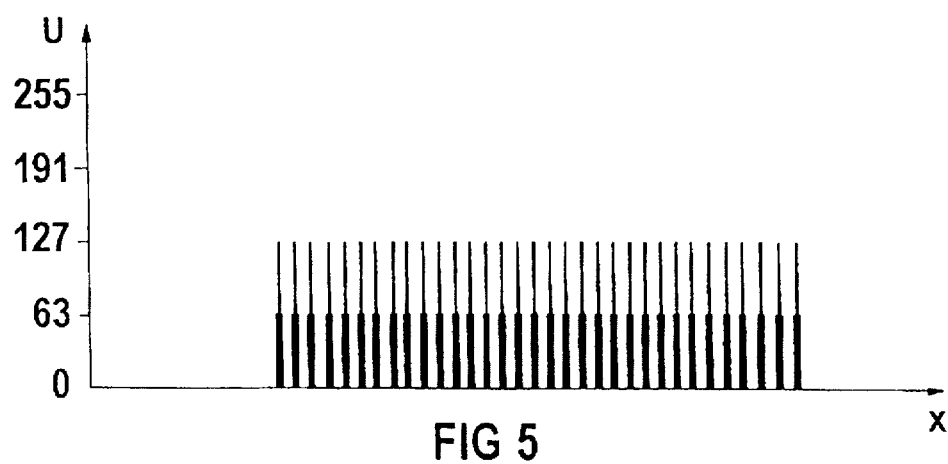
FIG. 5 shows output signals of the signal processing device, which have been corrected with regard to the signal spacing and the signal level.

FIG. 5 illustrates the signals resulting from a radiographic imaging of the test object 12, after the spacing correction signals and signal level correction signals have been taken into account. In other words, FIG. 5 illustrates a corrected radiographic measurement of the test object output by the signal processing device 4 operating in accordance with the correction methods described above.

It is self-evident that the corresponding correction signals can be produced not only for one row 6a of the radiation receiver 6 but for all the rows, and in particular for all the detector cells. However, it is also possible to form correction signals for a group of detector cells, or for columns, or for rows and columns of the radiation receiver.

In the above-mentioned procedure for correcting the vignetting effects, the same test object can be used as is used for correcting the geometric distortions. According to a variant of the invention, however, it is also possible to correct the vignetting effects either by introducing a test object 12 which is homogeneous to radiation into the radiation path or to dispense with a test object 12 altogether, so that the beam of radiation 11 is incident unimpeded on the radiation receiver 6.

Figure 6:
FIG. 6 shows the actual signals which are produced by a further test object and which can be derived from a row of the radiation receiver, without vignetting correction.

FIG. 6 shows, by way of example, a signal from the scanned row 6a of the radiation receiver 6 with or without such a test object 12. To correct the vignetting effect, a mean reference signal level $U_{av}$ is calculated from this signal from the row 6a, or, analogously, from signals taken from a selection of scanned rows, or columns, or from all the rows of the radiation receiver 6. Correction signals $\Delta U$ are then formed from the difference between the respective actual signal level U of a pixel signal, or a predetermined set of pixel signals of one or more or all the rows, and the reference signal level $U_{av}$, and are stored in the memory 19.

Figure 7:
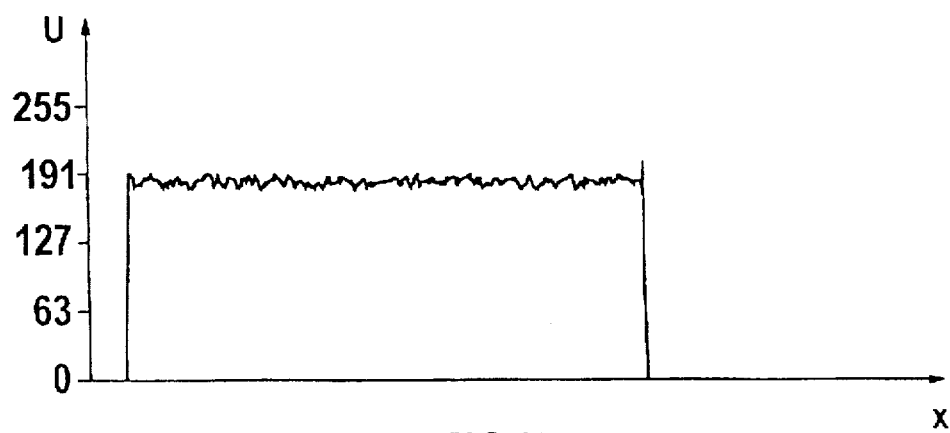
FIG. 7 shows the output signals of the signal processing device after the vignetting correction.

FIG. 7 shows a signal that can be obtained at the output of the signal processing device 4 following appropriate correction of the unprocessed signal, illustrated in FIG. 6, originating from row 6a of the radiation receiver 6.

C. Radiation Scanning

Figure 8:
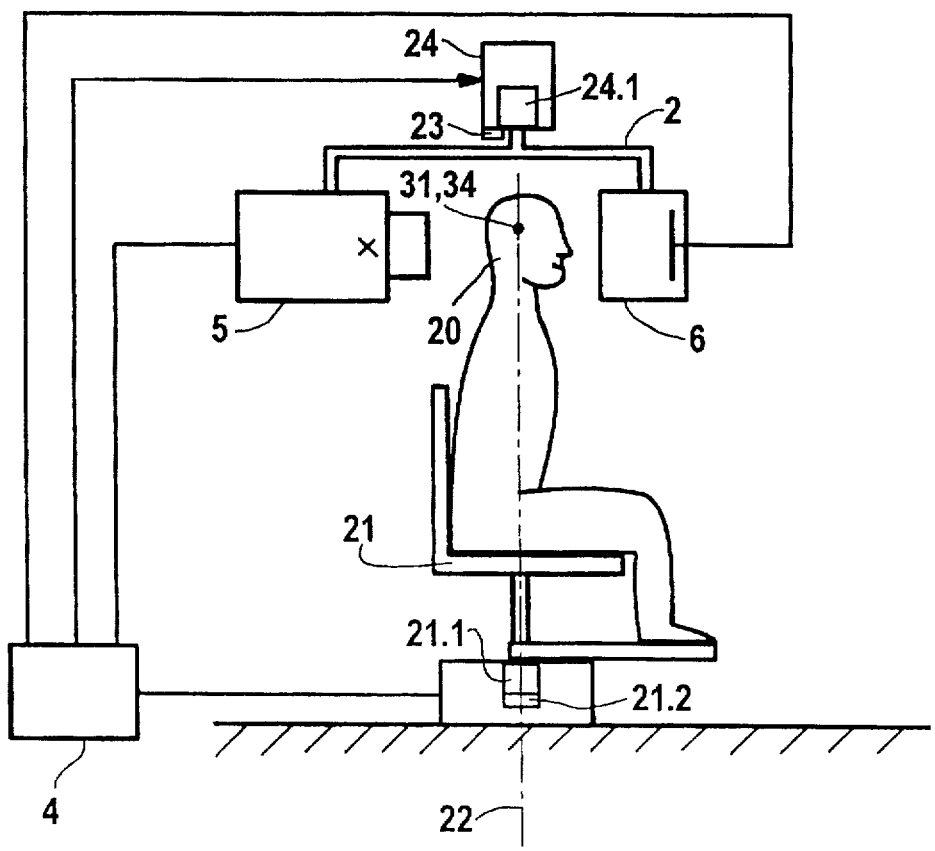
FIG. 8 is a schematic diagram of an X-ray diagnostic device according to a further exemplary embodiment of the invention.

The X-ray diagnostic device of FIG. 1 illustrates one example of an apparatus designed to perform a radiation scan of an object 20 to be examined, in accordance with the invention. In FIG. 1, the recording unit 2 orbits in a vertical plane. Alternatively, the recording unit 2, as shown in FIG. 8, can equally well be arranged in a horizontal plane, or in any other plane that facilitates the scanning procedure. To produce a relative displacement between a supporting device 21, having a drive 21.1 and a displacement pickup 21.2, and thus the object 20 to be examined, and the recording unit 2 having a bearing means 24 and a drive 24.1, as illustrated in FIG. 8, the recording unit 2 and/or the supporting device 21 are rotated through at least 180° about the vertical axis 22. It is likewise possible to move the supporting device 21 and the recording unit 2 in opposite directions relative to each other, so that in each case only half the displacement distance is necessary to achieve scanning. The X-ray diagnostic device shown in FIG. 8 is particularly suitable for dental diagnostic purposes.

To produce the above-mentioned image signals to be displayed on a display device, a processing unit (the CPU 16) must receive, in addition to the pixel signals from the radiation receiver 6, radiation direction signals $\Delta\Theta$ which represent the relative mutual orientation, over time, of the recording unit 2 in relation to the supporting device 1 or 21, and, in particular, in relation to the object 20 to be examined.

For this purpose, in a simple and advantageous refinement, a displacement pickup 23, for example a potentiometer, can be provided in order to detect a displacement of the C-frame-like mount 7 in relation to its bearing point 24.

Figure 9:
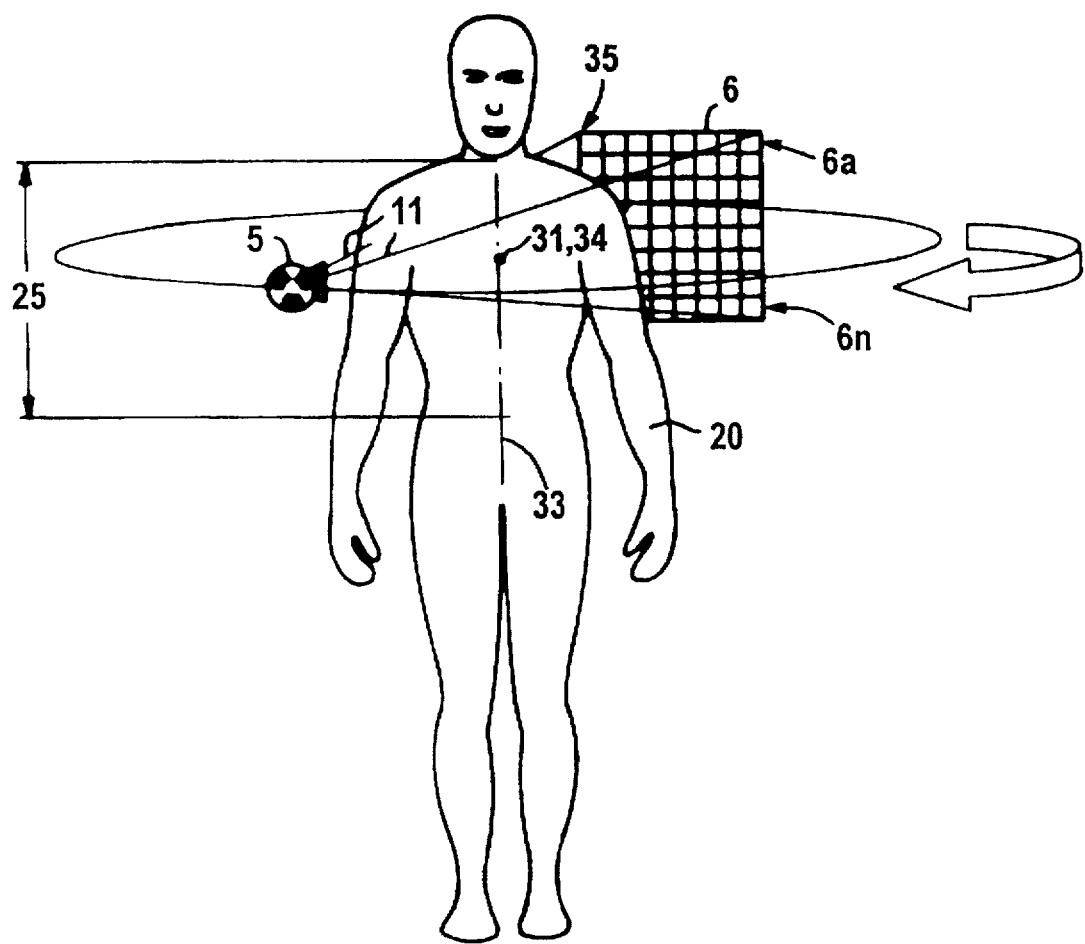
FIG. 9 shows the principle of scanning of an object to be examined.

As evident from FIG. 9, when scanning the object 20 with a beam of radiation 11 during an actual scan operation, the radiation shadow originating from a scanned cross section 25 of the object 20 being examined is incident on the detector elements of the radiation receiver 6. As already mentioned, the detector elements are read row by row, the row signals $I_R$ from one row thus representing the radiation shadow of a scanned cross-sectional plane $26_{(1-n)}$ (FIG. 10) of the object 20 being examined. The row signals $I_R$ are stored in conjunction with the signal $\Delta\Theta$ from the displacement pickup 23 in a row signal memory 27 of the signal processing device 4. For this purpose, for example, at each displacement of the recording unit 2 by an angle of 1°, radiation is emitted, the signals from the radiation receiver 6 are read row by row and are stored in the row signal memory 27. This procedure is repeated until the cross section 25 has been scanned at least through an angle of 180° and, preferably, in addition through the fan-out angle of the beam of radiation 11.

Figure 10:
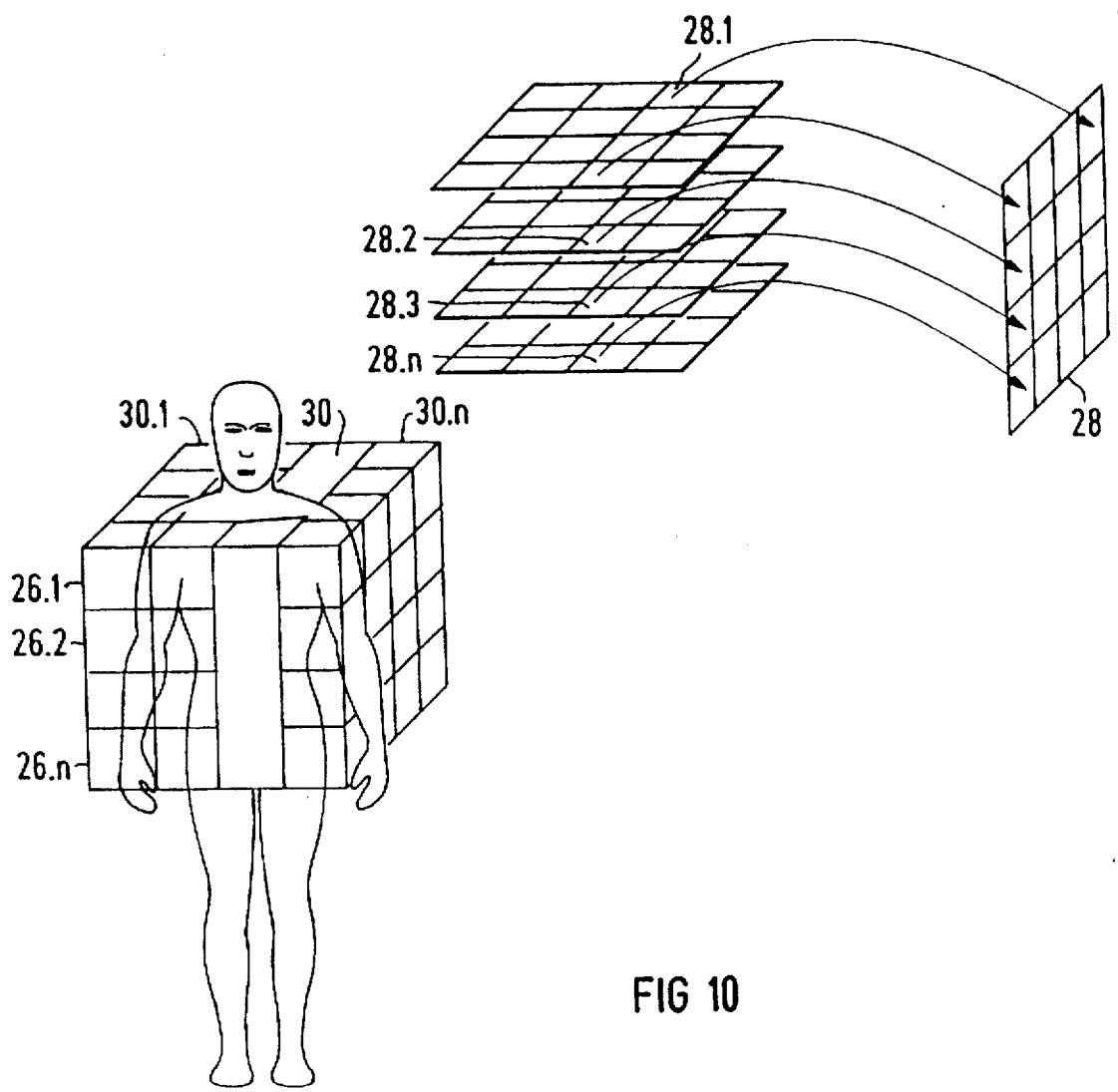
FIG. 10 shows, by way of example, calculable tomogram planes of a scanned cross section.

Calculation of the image signals for the object 20 being examined can proceed as follows. First, the CPU 16 accesses the signals IR stored in the row signal memory 27, and corrects these signals on the basis of the correction signals $\Delta S$, $\Delta U$ stored in the second and third memories 18, 19. From the corrected signals, the CPU 16 then calculates image signals for example for a selected sectional plane $28_{(1-n)}$ (FIG. 10). Accordingly, as a result of a single radiation scanning procedure for the cross section 25, and on the basis of the signals then stored in the row signal memory 27, image signals $I_p$ for any arbitrary sectional plane 28 can be calculated and can be stored in an image signal memory 29 of the signal processing device 4. For instance, from the signals stored in the row signal memory 27, it is possible for the CPU 16 to calculate not only image signals of a cross-sectional plane $28_{(1-n)}$, but also image signals of at least one sagittal plane $30_{(1-n)}$ (FIG. 10). Appropriate input of commands via the input device 10 can thus be used to cause image signals of any selected planes (e.g., 26, 28, 30) within the framework of the scanned cross section 25 to be calculated.

D. Signal Processing: Central Point of Rotation

In order to facilitate the operation of the X-ray diagnostic device and the production of the image signals, which can be displayed on a display device, of any arbitrarily selectable plane (e.g., 26, 28, 30), the X-ray diagnostic device of the present invention is operated according to a process in which, for example in a first process step, signals $P_c$, which can be stored in the memory 17 (or, alternatively, in some other memory) and which relate to the central point of rotation 31 of the radiation scan, are used in the calculation of the image signals I. In the exemplary embodiment, the central point of rotation 31 lies on the longitudinal axis 33 of the object 20 to be examined and in the isocenter 34 of the C-frame-like mount 7 (FIG. 9). The signals $P_c$ are required to provide a reference signal so as to link the different signals generated in a plurality of projections to a single point on or in the object.

According to a variant of the process, in the first process step, the signals $P_c$ relating to the central point of rotation 31 can be input to the memory 17 via the input device 10. According to a further variant, the first process step is performed as a radiation scan of a test object 12, and, thereafter, the CPU 16 evaluates signals obtained in the first process step, in order to determine the maximum spacing value $P_{max}$. The CPU 16 then calculates a mean spacing signal $P_{av}$ from the maximum spacing signal $P_{max}$ and feeds the calculated mean spacing signal $P_{av}$ to the first memory 17 as a signal of the central point of rotation 31, i.e., as the signal $P_c$. In this case it is advantageous if, in the first process step, the CPU 16 checks, on the basis of the radiation direction signals $\Delta\Theta$ from the displacement pickup 23, whether the signals of the maximum spacing $P_{max}$ are produced at radiation directions offset by 180° C. An object region of the object 20 to be examined having a characteristic radiation absorption can in this case be used as the test object 12.

E. Further Signal Processing

Figure 11:
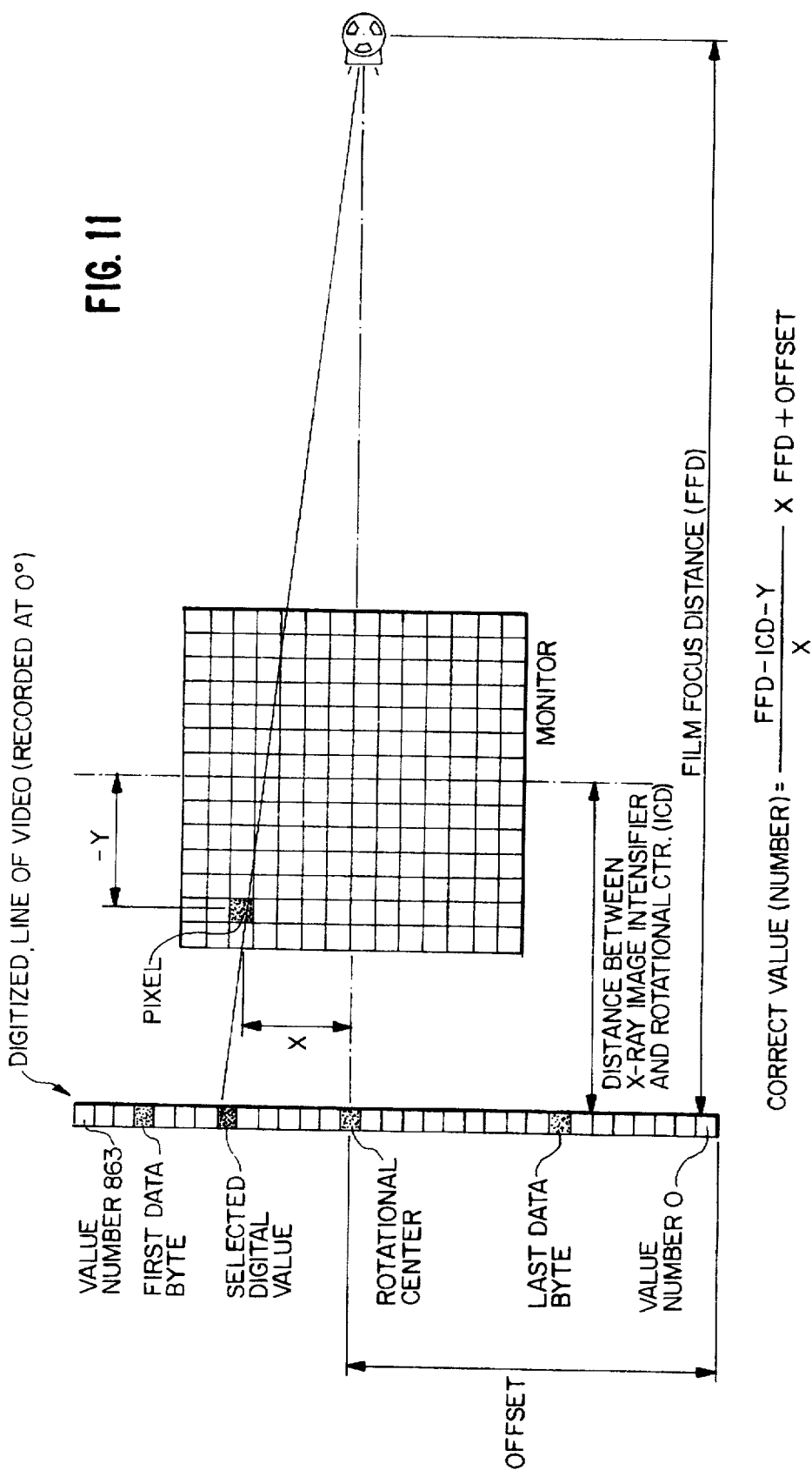
FIG. 11 shows the geometry underlying film-focus distance correction.

In a second, third or fourth process step, for example, the signals (ΔS, ΔU) stored in the second and third memories 18, 19 for correcting geometric distortions and/or for correcting vignetting effects and/or signals representing film-focus distance (FIG. 11) are used in the calculation of the image signals I. As already explained, these signals can be calculated by the signal processing device 4, or else can be input to the memory 17 via the input device 10. It should be noted, however, that the numeric designation of the process steps as given above need not define the actual sequence of operation.

Within the scope of the invention, in order to avoid unwanted effects, such as scattered radiation effects, in one process step the CPU can receive the signals from at least two rows 6a, 6b of the planar detector. From the pixel signals from the rows 6a, 6b that respectively correspond to some given column (see FIG. 9, at, e.g., 35) of the planar detector 6, the CPU calculates averaged pixel signals which, in a subsequent process step, can then be used in the calculation of the image signals of a cross-sectional plane 28, 30. From this it should be clear that use can be made not only of the signals from two rows 6a, 6b but also from any arbitrary selection of rows for the calculation of averaged pixel signals. Hence, unwanted effects which occur statistically distributed in particular can be reduced or essentially eliminated.

By means of the X-ray diagnostic device according to the invention it is possible to calculate not only tomographic planes in a cross-sectional plane of the object but, on the basis of the signals which are stored in the row signal memory 27, it is possible to calculate any arbitrarily selectable sectional planes 26, 28, 30, if the parameters of these sectional planes 26, 28, 30 are input to the signal processing device 4 via the input device 10.

In order to avoid disadvantageous scattered radiation effects in the production of signals, it is further advantageous if an adjustable anti-scattering grid 32 or a multi-line anti-scattering grid 32 is placed in front of the radiation receiver 6, which is designed as a planar detector.

What is claimed is:

1. A process for producing tomograms by means of an X-ray diagnostic device comprising:

a recording unit comprising a radiation transmitter, supported at one end of a C-frame-like mount, for transmitting a fan-shaped beam of radiation, and a planar detector, arranged as a radiation receiver, opposite the radiation transmitter, at another end of the C-frame-like mount, for receiving the beam of radiation and for producing electric signals;

a supporting device for an object to be examined;

means for producing a relative displacement between the recording unit and the supporting device during a radiation scanning procedure of the object in a cross section;

a signal transmitter for producing radiation direction signals as a function of the relative displacement; and a computing unit and at least one associated memory;

said process comprising:

inputting the electric signals of at least one row of the planar detector, obtained through the radiation scanning procedure, into the computing unit; and in the computing unit, calculating image signals for at least one sectional plane from the electric signals, obtained through the radiation scanning procedure, in conjunction with the radiation direction signals, the image signals being capable of being displayed as an image of the sectional plane on a display device;

wherein, in a first process step of said calculating step, signals relating to a central point of rotation of the radiation scanning procedure and stored in the memory are used in the calculation of the image signals.

2. The process as claimed in claim 1, further comprising: inputting the signals relating to the central point of rotation to the memory via an input device during the first process step.

3. The process as claimed in claim 1, further comprising: in the computing unit, evaluating signals obtained during a radiation scan of a test object, to determine a maximum spacing value for the radiation scan; calculating a mean spacing value from the maximum spacing value; and storing the calculated mean spacing value in the memory as the signals relating to the central point of rotation, during the first process step.

4. The process as claimed in claim 3, further comprising: in the computing unit, evaluating, based on the radiation direction signals, whether electric signals associated with the maximum spacing value are produced at respective radiation directions offset from one another by 180°.

5. The process as claimed in claim 3, wherein an object region of the object to be examined is used as the test object.

6. The process as claimed in claim 1, wherein, in a second process step of said calculating step, correction signals stored in memory for correcting vignetting effects are retrieved for use in the calculation of the image signals.

7. The process as claimed in claim 6, further comprising: inputting the correction signals into memory via an input device during the second process step.

8. The process as claimed in claim 6, wherein, in a third process step of said calculating step, correcting signals which are stored in memory for correcting geometric distortions are retrieved for use in the calculation of the image signals.

9. The process as claimed in claim 8, further comprising: inputting the correcting signals into memory via an input device during the third process step.

10. The process as claimed in claim 8, wherein, in a fourth process step of the calculating step, focus signals which are stored in memory and represent a film-focus spacing calculation parameter are retrieved for use in the calculation of the image signals.

11. The process as claimed in claim 10, further comprising: inputting the focus signals into memory via an input device during the third process step.

12. The process as claimed in claim 1, wherein, in a second process step of said calculating step, correcting signals which are stored in memory for correcting geometric distortions are retrieved for use in the calculation of the image signals.

13. The process as claimed in claim 12, further comprising: inputting the correcting signals into memory via an input device during the second process step.

14. The process as claimed in claim 12, wherein, in a third process step of the calculating step, focus signals which are stored in memory and represent a film-focus spacing calculation parameter are retrieved for use in the calculation of the image signals.

15. The process as claimed in claim 14, further comprising: inputting the focus signals into memory via an input device during the third process step.

16. The process as claimed in claim 1, wherein, in a second process step of the calculating step, focus signals which are stored in memory and represent a film-focus spacing calculation parameter are retrieved for use in the calculation of the image signals.

17. The process as claimed in claim 16, further comprising: inputting the focus signals into memory via an input device during the second process step.

18. The process as claimed in claim 1, further comprising:
  inputting arbitrarily selectable parameters of the cross section which has been scanned with radiation via an input device into the computing unit; and
  in the computing unit, calculating, on the basis of the input parameters, image signals of at least one sectional plane defined by the input parameters.

19. An X-ray device for producing tomograms, comprising:
  a recording unit comprising a radiation transmitter, supported at one end of a C-frame-like mount, for transmitting a fan-shaped beam of radiation, and a planar detector, arranged as a radiation receiver, opposite said radiation transmitter, at another end of said C-frame-like mount, for receiving the beam of radiation and for producing electric signals;
  a supporting device for an object to be examined;
  means for producing a relative displacement between said recording unit and said supporting device during a radiation scanning procedure of the object in a cross section;
  a signal transmitter for producing radiation direction signals as a function of the relative displacement;
  a computing unit, and at least one memory for storing image processing signals;
  wherein, as a result of the radiation scanning procedure, said computing unit receives the electric signals of at least one row of said planar detector;
  wherein said computing unit calculates image signals for at least one sectional plane from the electric signals received in conjunction with the radiation direction signals, the image signals being capable of being displayed as an image of the sectional plane on a display device; and
  wherein the image processing signals stored in said memory are retrieved for use in the calculation of the image signals.

20. The device as claimed in claim 19, wherein the electric signals of at least the one row of said planar detector are stored in said memory.

21. The device as claimed in claim 19, wherein the image processing signals stored in said memory include signals relating to a central point of rotation.

22. The device as claimed in claim 19, wherein the image processing signals stored in said memory include signals for correcting vignetting effects.

23. The device as claimed in claim 19, wherein the image processing signals stored in said memory include signals for correcting geometric distortions.

24. The device as claimed in claim 19, wherein the image processing signals stored in said memory include signals which represent film-focus spacing information.

25. The device as claimed in claim 19, wherein the image processing signals stored in said memory include:
  signals relating to a central point of rotation,
  signals for correcting vignetting effects,
  signals for correcting geometric distortions, and
  signals which represent film-focus spacing information.

26. The device as claimed in claim 19, further comprising: an input unit for inputting the image processing signals into said memory.

27. The device as claimed in claim 19, further comprising: an adjustable anti-scattering grid positioned over a radiation-receiving surface of said planar detector.

28. The device as claimed in claim 19, further comprising: a multi-line anti-scattering grid positioned over a radiation-receiving surface of said planar detector.

29. A process for producing tomograms by means of an X-ray diagnostic device comprising:
  a recording unit comprising a radiation transmitter, supported at one end of a C-frame-like mount, for transmitting a fan-shaped beam of radiation, and a planar detector, arranged as radiation receiver, opposite the radiation transmitter, at another end of the C-frame-like mount, for receiving the beam of radiation and for producing electric signals;
  a supporting device for an object to be examined;
  means for producing a relative displacement between the recording unit and the supporting device during a radiation scanning procedure of the object in a cross section;
  a signal transmitter for producing radiation direction signals as a function of the relative displacement; and
  a computing unit;
said process comprising:
  inputting the electric signals of at least two rows of the planar detector as pixel signals into the computing unit;
  in a first process step of the computing unit, producing averaged pixel signals from respective ones of the pixel signals that are assigned to a column of the planar detector that is common to the respective ones of the pixel signals; and
  in a subsequent process step of the computing unit, calculating from the averaged pixel signals image signals for at least one sectional plane, the image signals being capable of being displayed as an image of the sectional plane on a display device.

30. The process as claimed in claim 29, further comprising:
  inputting arbitrarily selectable parameters of the cross section which has been scanned with radiation via an input device into the computing unit; and
  in the computing unit, calculating, on the basis of the input parameters, image signals of at least one sectional plane defined by the input parameters.

31. An X-ray device for producing tomograms, comprising:
  a recording unit comprising a radiation transmitter, supported at one end of a C-frame-like mount, for transmitting a fan-shaped beam of radiation, and a planar detector, arranged as a radiation receiver, opposite said radiation transmitter, at another end of said C-frame-like mount, for receiving the beam of radiation and for producing electric signals at pixel locations arranged in rows and columns;
  a supporting device for an object to be examined;
  means for producing a relative displacement between said recording unit and said supporting device during a radiation scanning procedure of the object in a cross section;

a signal transmitter for producing radiation direction signals as a function of the relative displacement; and a computing unit;

wherein, as a result of the radiation scanning procedure, said computing unit receives the electric signals of at least two rows of said planar detector as pixel signals;

wherein said computing unit produces averaged pixel signals from respective ones of the pixel signals that are assigned to a column of said planar detector that is common to the respective ones of the pixel signals; and wherein said computing unit calculates, from the averaged pixel signals, image signals for at least one sectional plane, the image signals being capable of being displayed as an image of the sectional plane on a display device.

32. The device as claimed in claim 31, further comprising:

an input device for inputting arbitrarily selectable parameters of the cross section which has been scanned with radiation into said computing unit; and wherein said computing unit calculates, on the basis of the input parameters, image signals of at least one sectional plane defined by the input parameters.

33. A process for producing tomograms by means of an X-ray diagnostic device comprising a recording unit, a supporting device, and a processing unit, the recording unit comprising a C-frame-shaped mount, a radiation transmitter, supported at a first end of the C-frame-shaped mount, and a planar detector, provided as a radiation receiver and supported opposite the radiation transmitter at a second end of the C-frame-shaped mount, and the supporting device being configured to support an object to be examined, said process comprising:

transmitting divergent beams of radiation from the radiation transmitter, receiving the beams of radiation at the planar detector, and converting the received beams into electrical signals, for at least one row of the planar detector;

during said transmitting, receiving and converting step, displacing the recording unit relative to the supporting device for the purpose of producing a cross-sectional radiation scan of the object to be examined, the radiation scan being characterized by a central point of rotation;

producing radiation direction signals indicative of the relative displacement;

inputting the electrical signals of the planar detector for at least the one row of the planar detector to the processing unit;

inputting signals defining the central point of rotation of the radiation scan to the processing unit;

in the processing unit, calculating image signals for at least one sectional plane on the basis of the electrical signals, the radiation direction signals and the signals defining the central point of rotation of the radiation scan, whereby the calculated image signals can be used for producing an image of the sectional plane on a display device connected to the processing unit.

34. The process according to claim 33, further comprising:

in the processing unit, correcting the image signals in accordance with correction signals input to the processing unit, wherein the correction signals are:

signals for correcting geometrical distortions in the image of the sectional plane, signals for correcting signal-level distortions in the image of the sectional plane, or signals for averaging at least some of the electrical signals over at least a predetermined portion of the planar detector.

35. The process according to claim 34, further comprising:

prior to producing the radiation scan of the object to be examined, generating the signals for correcting geometrical distortions by comparing reference spacing signals with actual spacing signals, wherein the actual spacing signals are generated by transmitting at least one test beam of radiation through a test object, receiving the test beam, and converting the test beam into the actual spacing signals.

36. The process according to claim 34, further comprising:

prior to producing the radiation scan of the object to be examined, generating the signals for correcting geometrical distortions by transmitting at least one test beam of radiation through a test object having regions of contrasting radiation absorption arranged in a regular pattern, receiving the test beam, converting the test beam into actual spacing signals, calculating an average spacing signal from the actual spacing signals, and comparing the average spacing signal with the actual spacing signals.

37. The process according to claim 34, further comprising:

prior to producing the radiation scan of the object to be examined, generating the signals for correcting signal-level distortions by comparing a reference signal-level signal with actual signal-level signals, wherein the actual signal-level signals are generated by transmitting at least one test beam of radiation, receiving the test beam, and converting the test beam into the actual signal-level signals.

38. The process according to claim 34, further comprising:

prior to producing the radiation scan of the object to be examined, generating the signals for correcting signal-level distortions by transmitting at least one test beam of radiation, receiving the test beam, converting the test beam into actual signal-level signals, calculating an average signal-level signal from the actual signal-level signals, and comparing the average signal-level signal with the actual signal-level signals.

39. The process according to claim 33, wherein the radiation scan is further characterized by a major axis and by a plurality of displacement locations, said process further comprising:

determining at least one subset of the electrical signals corresponding to any of the displacement locations that intersect the major axis;

calculating a mid-point signal representing a mid-point on the major axis of the radiation scan; and storing the mid-point signal in memory as the signals defining the central point of rotation.

40. The process according to claim 39, further comprising:

performing a self-diagnostic routine by using the radiation direction signals in order to determine whether the one subset of the electrical signals correspond to radiation directions offset by 180°.

41. An X-ray diagnostic system for producing tomograms, comprising:

a C-frame-shaped mount;

a radiation transmitter, supported at a first end of said C-frame-shaped mount, for transmitting divergent beams of X-ray radiation;

a planar detector, provided as a radiation receiver having a matrix surface defined by rows and columns and supported opposite said radiation transmitter at a second end of said C-frame-shaped mount, for converting the received beams of X-ray radiation into electrical signals;

a supporting device configured to support an object to be examined;

means for displacing said radiation transmitter relative to said supporting device for the purpose of producing a cross-sectional radiation scan of the object to be examined, the radiation scan being characterized by a central point of rotation;

a detector for producing radiation direction signals indicative of the relative displacement; and a computing unit, and at least one memory for storing image processing signals, said computing unit being configured to:

receive the electrical signals from said planar detector for at least the one row of said planar detector, receive the radiation direction signals, and receive signals defining the central point of rotation of the radiation scan; and calculate image signals for at least one sectional plane on the basis of the electrical signals, the radiation direction signals and the signals defining the central point of rotation of the radiation scan, whereby the calculated image signals can be used for producing an image of the sectional plane on a display device connected to the processing unit.

42. The system according to claim 41, wherein, during the radiation scan, said C-frame-shaped mount stepwise traverses an arcuate path extending through an angle of substantially 180° about an isocenter of said C-frame-shaped mount.

43. The system according to claim 41, wherein the angle of substantially 180° consists essentially of 180° plus an angle of divergence of the divergent beams of X-ray radiation.

* * * * *